United States Patent [19]

Orvik et al.

[11] Patent Number: 4,705,859

[45] Date of Patent: Nov. 10, 1987

[54] POLYCHLOROPYRIDINE PRODUCTION FROM POLYCHLORO-2,3-LUTIDINES

[75] Inventors: Jon A. Orvik, Walnut Creek; Thomas J. Dietsche, Berkeley, both of Calif.

[73] Assignee: The Dow Chemical Company, Midland, Mich.

[21] Appl. No.: 889,052

[22] Filed: Jul. 22, 1986

[51] Int. Cl.$^4$ .......................................... C07D 211/72
[52] U.S. Cl. .................................................... 546/345
[58] Field of Search ........................................ 546/345

[56] References Cited

U.S. PATENT DOCUMENTS

| | | | |
|---|---|---|---|
| 3,186,994 | 6/1965 | Johnston et al. | 546/345 |
| 3,420,833 | 1/1969 | Taplin | 546/345 |
| 3,538,100 | 11/1970 | Smith | 546/345 |
| 3,709,894 | 1/1973 | Klemm et al. | 546/345 |
| 3,732,230 | 5/1973 | Brewer et al. | 546/345 |
| 4,227,001 | 10/1980 | Dietsche et al. | 546/345 |
| 4,256,894 | 3/1981 | Dietsche et al. | 546/345 |
| 4,483,993 | 11/1984 | Marinak | 546/345 |
| 4,507,486 | 3/1985 | Marinak | 546/345 |
| 4,563,531 | 1/1986 | Marinak et al. | 546/345 |
| 4,577,027 | 3/1986 | Marinak | 546/345 |

OTHER PUBLICATIONS

Tsuda et al., Pharm. Bull., Japan, 1, 142-5, (1953), CA-50 13895i, (1956).

Primary Examiner—Henry R. Jiles
Assistant Examiner—Robert C. Whittenbaugh
Attorney, Agent, or Firm—D. Wendell Osborne

[57] ABSTRACT

Polychloropyridines containing chlorine substituents in the 2, 3, and 6 positions and, optionally, in the 4 and 5 positions, are prepared from polychloro-2,3-lutidines containing at least one chlorine substituent in each methyl group and, optionally, a chlorine substituent in the 6 position by liquid phase chlorination. Lewis acid metal halide catalysts are, optionally, employed. 2,3,5,6-Tetrachloropyridine is, accordingly, prepared by chlorination at about 200° to about 260° C. in the presence of ferric chloride catalyst of a mixture of polychloro-2,3-lutidines obtained by the vapor phase chlorination of 2,3-lutidine.

31 Claims, No Drawings

POLYCHLOROPYRIDINE PRODUCTION FROM POLYCHLORO-2,3-LUTIDINES

BACKGROUND OF THE INVENTION

Polychloropyridines are valuable intermediates in the production of a wide variety of agricultural insecticides, herbicides, fungicide, and many other useful materials. Several polychloropyridines have been produced commercially and a number of processes for their production have been described. These known processes generally involve the chlorination of pyridine or a compound containing a pyridine nucleus. Methods for the chlorination of pyridine to polychloropyridines are revealed, for example, in U.S. Pat. Nos. 3,732,230 and 3,420,833. The chlorination of akyl pyridines in the vapor phase to obtain pentachloropyridine is further taught in U.S. Pat. No. 3,420,833. The chlorination in the liquid phase of alpha-picoline, beta-picoline, and 3,5-lutidine to obtain certain polychloropyridines is shown in U.S. Pat. Nos. 4,577,027, 4,483,993, and 4,507,486, respectively. Certain metal halide catalysts are sometimes employed ln these processes. 2,6-Dichloropyridine is converted to 2,3,5,6-tetrachloropyridine and pentachloropyridine by liquid phase chlorination in the presence of selected metal halide catalysts according to U.S. Pat. No. 3,538,100. The liquid phase chlorination of various chlorinated (trichloromethyl)pyridines to obtain certain polychloropyridines is discussed in U.S. Pat. Nos. 3,186,994, 4,256,894, 4,563,531, and 4,483,993. The use of uv light and of specific metal halide catalysts is optionally employed in some of these processes.

The present invention relates to the preparation of a select class of polychloropyridines by the chlorination of certain polychloro-2,3-lutidines.

SUMMARY OF THE INVENTION

It has now been found that the liquid phase chlorination of partially chlorinated 2,3-lutidines in which both methyl groups and, optionally, the 6 position of the ring contain chlorine substituents, is a convenient and economical process for the production of polychloropyridines in which the 2, 3, and 6 positions and, optionally, the 4 and 5 positions are substituted by chlorine.

Thus, polychloropyridines of Formula I

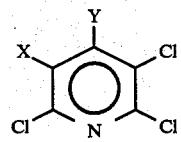

(I)

wherein X and Y each, independently represents H or Cl are prepared in a process which comprises contacting a polychloro-2,3-lutidine of Formula II

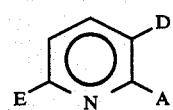

(II)

wherein
A and D each, independently represents mono-, di-, or trichloromethyl; and
E represents H or Cl with chlorine in the liquid phase under conditions conducive to chlorination.

The preparation of 2,3,5,6-tetrachloropyridlne and pentachloropyridine by the process is facilitated by Lewis acid metal halide catalysts whereas the preparation of 2,3,6-trichloropyridine is best conducted in the absence of such catalysts.

In a preferred embodiment of the process, a mixture of polychloro-2,3-lutidines as defined hereinabove, which was obtained by the vapor phase chlorination of 2,3-lutidine, is contacted with excess chlorine in the liquid phase in the presence of ferric chloride catalyst at about 200° C. to about 260° C. to obtain a mixture of polychloropyridines containing 2,3,5,6-tetrachloropyridine as a major component. The 2,3,5,6-tetrachloropyridine is recovered from the reaction mixture by distillation.

DETAILED DESCRIPTION OF THE INVENTION

The polychloropyridines prepared in the present invention are defined by Formula I. These polychloropyridines are characterized by having chlorine substition in the 2, 3, and 6 positions and, optionally, in the 4 and 5 positions. The compounds included in this definition are 2,3,6-trichloropyridine, 2,3,5,6-tetrachloropyridine, 2,3,4,6-tetrachloropyridine, and pentachloropyridine.

The polychloro-2,3-lutidines that are employed as starting materials in the present invention are defined by Formula II. They are characterized as 2,3-lutidines substituted by at least one chlorine atom on each methyl group and optionally by chlorine in the 6 position of the ring. These compounds can be employed in the process individually or as mixtures containing two o more of them.

The polychloro-2,3-lutidines of Formula II can be obtained by the vapor phase chlorination of 2,3-lutidine (see Ser. No. 888,897, filed July 22, 1986). A mixture of polychloro-2,3-lutidines obtained by the vapor phase chlorination of 2,3-lutidine can be used in the present process without further purification either before or after the removal of any chlorocarbon diluent. Alternatively, such mixtures can be separated lnto individual compounds of Formula II and any or all of the individual compounds thus obtained can be utilized separately. The compounds of Formula 11 typically obtained in this manner include 2-(chloromethyl)-3-(dichloromethyl)pyridine, 3-(chloromethyl)-2-(dichloromethyl)pyridine, 2,3-bis(dichloromethyl)pyridine, 6-chloro-2,3-bis(dichloromethyl)pyridine, 3-(dichloromethyl)-2-(trichloromethyl)pyridine, 6-chloro-3-(dichloromethyl)-2-(trichloromethyl)pyridine, and 6-chloro-2-(dichloromethyl)-3-(trichloromethyl)pyridine.

The compounds of Formula II wherein A and D each represents chloromethyl can also be prepared by the methods revealed in Pharm. Bull. (Japan), 1, 142–5, (1953); and in U.S. Pat. No. 3,709,894.

The chlorination reactions that take place on contacting polychloro-2,3-lutidines of Formula II with chlorine under the conditions of the present invention are the replacement of ring and mono- or dichloromethyl substituent hydrogen atoms by chorine and the replacement of trichloromethyl groups by chlorine. In order to obtain the products of the present invention, both of the chlorinated methyl groups and up to three of the ring hydrogen atoms of the polychloro-2,3-lutidines of Formula II must be replaced by chlorine.

The process of the present invention can be carried out in any equipment suitable for liquid phase chlorination. Such equipment is well known to those skilled in the art. It can be carried out batch-wise using one or more chlorination reactors or in a continuous manner, such as that described in U.S. Pat. No. 4,256,894.

In carrying out the invention, the polychloro-2,3-lutidine of Formula II, chlorine, and, optionally, a catalyst are placed in a reaction vessel and the mixture is heated. The reactants can be added in any order and the heat can be applied before or after the addition of any of the reactants. It is generally preferred to place the polychloro-2,3-lutidine and any catalyst in the reaction vessel, heat as required to obtain a molten mass, add chlorine, and finally heat to the desired reaction temperature.

Chlorine is employed in the present process in an amount at least sufficient to convert all of the chlorinated methyl moieties to carbon tetrachloride and to place the desired number of chlorine atom substituents on the polychloropyridine product. Typically an excess is employed as this tends to facilitate the process.

Lewis acid metal halide catalysts can be employed in the process to accelerate the reactions involved, especially the reactions involving replacement of the 5-position hydrogen atom of the polychloro-2,3-lutidine starting materials by chlorine. Useful catalysts include the halides of iron, zinc, aluminum, tantalum, antimony, tungsten, molybdenum, titanium, nickel, cobalt, and the like. The chlorides are generally the preferred halides and iron is the preferred metal of the salt. Ferric chloride is especially preferred. The metal halide catalyst can be added in the form of a metal in those cases, such as iron, zinc, and aluminum, where the metal is converted to the corresponding metal chloride under the reaction conditions or can be added in the form of a metal oxide or oxyhalide in those cases where the metal oxide or oxyhalide is converted to the corresponding metal chloride under the reaction conditions. The addition of iron in lieu of ferric chloride is a preferred procedure.

Lewis acid metal halide catalysts, when employed, are employed in an amount sufficient to accelerate the chlorination. Generally, amounts up to six percent by weight of the polychloro-2,3-lutidine starting material are appropriate. Amounts of about 1 to about 5 percent are preferred. Such catalysts are generally employed when the desired polychloropyridine product is primarily 2,3,5,6-tetrachloropyridine or pentachloropyridine and are generally not employed when the desired product is primarily 2,3,6-trichloropyridine or 2,3,4,6-tetrachloropyridine.

Hydrogen chloride is formed as a by-product in the process and is, therefore, present during the process. It is, however, often helpful to the process to add additional hydrogen chloride to the reaction mixture either before the introduction of chlorine or concurrently with the introduction of chlorine.

The polychloropyridines of Formula I are generally formed when polychloro-2,3-lutidines of Formula II are contacted with chlorine at temperatures above about 160° C. Increasing the temperature increases the reaction rate and generally increases the degree of chlorination. That is to say the reaction produces more tetra- and pentachloropyridines and less 2,3,6-trichloropyridine at higher temperatures. Reaction temperatures of about 180° C. to about 300° C. are preferred and temperatures of about 200° C. to about 260° C. are especially preferred. In the case of continuous processes or batch processes using multiple reactors, it is often advantageous to employ different temperatures downstream or in the latter reactors than the temperatures used for the original contact of chlorine and compounds of Formula II.

The process of the present invention can be carried out at atmospheric or super-atmospheric pressure. Super atmospheric pressures are often preferred because such pressures facilitate the contact of the polychloro-2,3-lutidines with chlorine, allow the reactor to contain more chlorine, and thereby accelerate the reactions. It also allows the use of reaction temperatures above the boiling point of any reaction mixture component. Pressures up to about 400 psig are normally employed and it is often preferred to employ pressures of about 15 to about 300 psig. Pressures of about 200 psig are especially preferred.

The reaction mixtures are optionally agitated throughout the chlorination or during some part of it.

The chlorination reaction is continued until a substantial amount of the desired polychloropyridine of Formula I has formed or until a substantial portion of the polychloro-2,3-lutidine of Formula II has been converted to polychloropyridines. This generally requires several hours to several days depending on the amount of chlorine employed, the presence, amount and identity of any catalyst, the temperature, the pressure, and the other parameters employed. The reaction can be monitored using standard analytical techniques such as gas chromatography, liquid chromatography, and the like to determine the course of the reaction and its status at any time. The desired reaction conclusion time can thus be determined. The reaction is terminated by ceasing to heat and releasing any pressure in the reactor.

The present process can be optimized readily by one skilled in the art for the production of any polychloropyridine of Formula I using any polychloro-2,3-lutidine of Formula II as the starting material by adjusting the parameters discussed herein and following the progress of the reaction by standard analytical techniques as noted above.

The polychloropyridines of Formula I are generally obtained in the process of the present invention as mixtures containing at least one such compound. The individual compounds of Formula I can be recovered from the reaction mixture by standard methods such as distillation, crystallization, and extraction. It is generally preferred to isolate the products by distillation. Multiple distillations carried out in series are often employed.

The following examples are presented to illustrate the invention and should not be construed as limiting.

EXAMPLE 1 —NON-CATALYTIC CHLORINATION OF A MIXTURE OF POLYCHLORO-2,3-LUTIDINES

A 30 g sample of mixed polychloro-2,3-lutidines containing the following approximate percentage composition: 2,3-bis(dichloromethyl)pyridine, 2.2; 6-chloro-2,3-bis(dichloromethyl)pyridine and 3-(dichloromethyl)-2-(trichloromethyl)pyridine, 13.6; 6-chloro-2-(dichlormethyl)-3-(trichloromethyl)pyridine and 6-chloro-3-(dichloromethyl)-2-(trichloromethyl)pyridine, 45.3; unknown $C_7H_2Cl_7N$ (2 components), 1.8; 3,6-dichloro-2-(trichloromethyl)pyridine, 6.8; 2,6-dichloro-3-(trichloromethyl)pyridine, 10.6; 2,3,6-trichloropyridine, 6.3; 2,3,4,6-tetrachloropyridine, 0.8; 2,3,5,6-tetrachloropyridine, 0.5; and pentachlorovinylpyridines (2 components), 11.9 was placed in a 50 ml round bottom flask fitted with a condenser, scrubber, and dip tube for introducing chlorine. The flask was heated to about 165° C. and chlorine was introduced at the rate of about 35 mmoles per hour. Heating and chlorine addition were continued at about 165° C. for about 3 hours. The chlorine addition was continued and the temperature was increased to about 200° C. for about 12 hours and then to about 245° C. for an additional approximately 15 hours. Analysis of the reaction mixture by capillary gas chromatography using standards showed that it contained the following approximate percentage composition: 2,3,6-trichloropyridine, 53.6; 2,3,4,6-tetrachloropyridine, 3.4; 2,3,5,6-tetrachloropyridine, 8.8; pentachloropyridine, 0.7; 3,6-dichloro-2-(trichloromethyl)-pyridine, 4.8; 2,6-dichloro-3-(trichloromethyl)pyridine, 16.2; 3,5,6-trichloro-2-(trichloromethyl)pyridine, 0.4; 2,5,6-trichloro-3-(trichloromethyl)pyridine, 1.5; and hexachloro-2,3-lutidines, 1.9. A total of 8.1 g of carbon tetrachloride was collected in the scrubber.

EXAMPLE 2 —CATALYTIC CHLORINATION OF A MIXTURE OF POLYCHLORO-2,3-LUTIDINES

A 30 g sample of the mixture of polychloro-2,3-lutidines employed in Example 1 was placed in a 50 ml round bottom flask fitted with a condenser, scrubber and dip tube for introducing chlorine. Ferric chloride (0.45 g, 1.5 weight percent) was added and the resulting mixture was heated to about 200° C. Chlorine was introduced at the rate of about 35 mmoles per hour and continued for about 2 hours at about 200° C. and 25 hours at about 245° C. Analysis of the reaction mixture by capillary gas chromatography using standards showed that it contained the following percentage composition: 2,3,6-trichloropyridine, 5.9; 2,3,4,6-tetrachloropyridine, 1.8; 2,3,5,6-tetrachloropyridine, 62.0; pentachloropyridine, 11.9; 2,6-dichloro-3-(trichloromethyl)pyridine, 1.2; 2,5,6-trichloro-3-(trichloromethyl)pyridine, 6.3; and hexachlorolutidines, 2.2. A total of over 7.1 g of carbon tetrachloride was collected in the scrubber.

We claim:

1. A process for preparing a polychloropyridine of the formula

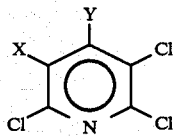

wherein X and Y each, independently represents H or Cl
which comprises contacting a polychloro-2-3-lutidine of the formula

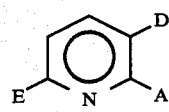

wherein
A and D each, independently represents mono-, di- or trichloromethyl, with the proviso that at least one of A and D is other than trichloromethyl; and E represents H or Cl
with chlorine in the liquid phase under conditions conducive to chlorination.

2. A process according to claim 1 wherein the contacting is conducted in the presence of a Lewis acid metal halide catalyst.

3. A process according to claim 2 wherein the catalyst is ferric chloride.

4. A process according to claim 2 wherein the catalyst is employed in an amount up to about six percent by weight of the polychloro-2,3-lutidine present.

5. A process according to claim 1 wherein the polychloro-2,3-lutidine is employed as a mixture comprising at least two polychloro-2,3-lutidines.

6. A process according to claim 5 wherein the mixture is a reaction mixture obtained by vapor phase chlorination of 2,3-lutidine.

7. A process according to claim 1 wherein the polychloro-2,3-lutidine is selected from the group consisting of 2-(chloromethyl)-3-(dichloromethyl)pyridine, 3-(chloromethyl)-2-(dichloromethyl)pyridine, 2,3-bis(dichloromethyl)pyridine, 6-chloro-2,3-bis(dichloromethyl)pyridine, 3-(dichloromethyl)-2-(trichloromethyl)pyridine, 6-chloro-3-(dichloromethyl)-2-(trichloromethyl)pyridine, and 6-chloro-2-(dichloromethyl)-3-(trichloromethyl)pyridine.

8. A process according to claim 1 wherein the polychloropyridine prepared is 2,3,5,6-tetrachloropyridine.

9. A process according to claim 1 wherein the polychloropyridine prepared is 2,3,6-trichloropyridine.

10. A process according to claim 1 wherein the polychloropyridine prepared is pentachloropyridine.

11. A process according to claim 1 wherein the contacting is conducted at a pressure of up to about 400 psig.

12. A process according to claim 11 wherein the pressure is about 15 to about 300 psig.

13. A process according to claim 1 wherein the contacting is conducted at a temperature above about 160° C.

14. A process according to claim 13 wherein the temperature is about 180° C. to about 300° C.

15. A process according to claim 1 wherein the polychloropyridine is additionally recovered from the reaction mixture prepared.

16. A process according to claim 15 wherein the recovery comprises distilling.

17. A process according to claim 1 which is conducted in a batch-wise operation.

18. A process according to claim 1 which is conducted in a continuous operation.

19. A process for preparing 2,3,5,6-tetrachloropyridine which comprises contacting a polychloro-2,3-lutidine of the formula

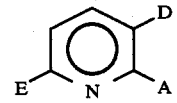

wherein
A and D each, indenpendently represents mono-, di-, or trichloromethyl, with the proviso that at least one of A and D is other than trichloromethyl; and
E represents H or Cl with chlorine in the liquid phase in the presence of a Lewis metal halide catalyst under conditions conducive to the formation of 2,3,5,6-tetrachloropyridine.

20. A process according to claim 19 wherein the catalyst is ferric chloride.

21. A process according to claim 19 wherein the polychloro-2,3-lutidine is employed as a mixture comprising at least two polychloro-2,3-lutidines.

22. A process according to claim 21 wherein the mixture is a reaction mixture obtained by vapor phase chlorination of 2,3-lutidine.

23. A process according to claim 19 wherein the polychloro-2,3-lutidine is selected from the group consisting of 2-(chloromethyl)-3-(dichloromethyl)pyridine, 3-(chloromethyl)-2-(dichloromethyl)pyridine, 2,3-bis(-dichloromethyl)pyridine, 6-chloro-2,3-bis(dichloromethyl)pyridine, 3-(dichloromethyl)-2-(trichloromethyl)-pyridine, 6-chloro-3-(dichloromethyl)-2-(trichloromethyl)pyridine, and 6-chloro-2-(dichloromethyl)-3-(trichloromethyl)pyridine.

24. A process according to claim 19 wherein 2,3,5,6-tetrachloropyridine is additionally recovered from the reaction mixture prepared.

25. A process according to claim 24 wherein the recovery comprises distilling.

26. A process for preparing 2,3,6-trichloropyridine which comprises contacting a polychloro-2,3-lutidine of the formula

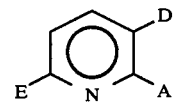

wherein
A and D each, independently represents mono-, di-, or trichloromethyl, with the proviso that at least one of A and D is other than trichloromethyl; and
E represents H or Cl
with chlorine in the liquid phase in the absence of a Lewis acid catalyst under conditions conducive to the formation of 2,3,6-trichloropyridine.

27. A process according to claim 26 wherein the polychloro-2,3-lutidine is employed as a mixture comprising at least two polychloro-2,3-lutidines.

28. A process according to claim 27 wherein the mixture is a reaction mixture obtained by vapor phase chlorination of 2,3-lutidine.

29. A process according to claim 26 wherein the polychloro-2,3-lutidine is selected from the group consisting of 2-(chloromethyl)-3-(dichloromethyl)pyridine, 3-(chloromethyl)-2-(dichloromethyl)pyridine, 2,3-bis(-dichloromethyl)pyridine, 6-chloro-2,3-bis(dichloromethyl)pyridine, 3-(dichloromethyl)-2-(trichloromethyl)-pyridine, 6-chloro-3-(dichloromethyl)-2-(trichloromethyl)pyridine, and 6-chloro-2-(dichloromethyl)-3-(trichloromethyl)pyridine.

30. A process according to claim 26 wherein the 2,3,6-trichloropyridine is additionally recovered from the reaction mixture prepared.

31. A process according to claim 30 wherein the recovery comprises distilling.

* * * * *

UNITED STATES PATENT AND TRADEMARK OFFICE
CERTIFICATE OF CORRECTION

PATENT NO. : 4,705,859

DATED : November 10, 1987

INVENTOR(S) : Jon A. Orvik; Thomas J. Dietsche

It is certified that error appears in the above-identified patent and that said Letters Patent is hereby corrected as shown below:

Col. 1, line 7, "intermediates" has been misspelled;

Col. 1, line 9, "fungicides" has been misspelled;

Col. 1, line 17, "alkyl" has been misspelled;

Col. 1, line 24, after the word "employed" the word should be -- in --;

Col. 2, line 3, "2,3,5,6-tetrachloropyridine" has been misspelled;

Col. 2, line 24, "substitution" has been misspelled;

Col. 2, line 35, delete "o" and insert therefore the word -- or --;

Col. 2, line 44, "into" has been misspelled;

Col. 2, line 47, delete "11" and insert therefore -- II --;

UNITED STATES PATENT AND TRADEMARK OFFICE
CERTIFICATE OF CORRECTION

PATENT NO. : 4,705,859

DATED : November 10, 1987

INVENTOR(S) : Jon A. Orvik; Thomas J. Dietsche

It is certified that error appears in the above-identified patent and that said Letters Patent is hereby corrected as shown below:

Col. 2, line 63, "chlorine" has been misspelled;

Col. 3, line 5, "continuous" has been misspelled;

Col. 4, lines 61-62, "6-chloro-2-(dichloromethyl)-3-(trichloromethyl)pyridine" has been misspelled;

Col. 5, lines 13-14, "2,3,4,6-tetrachloropyridine" has been misspelled;

Col. 6, line 65, "independently" has been misspelled.

Signed and Sealed this

Twenty-ninth Day of November, 1988

Attest:

DONALD J. QUIGG

*Attesting Officer*    Commissioner of Patents and Trademarks